United States Patent [19]

Furia et al.

[11] 3,961,054
[45] June 1, 1976

[54] COMBATTING DANDRUFF WITH MERCAPTO QUINOLINE N-OXIDES

[75] Inventors: Thomas E. Furia, Hartsdale; David H. Steinberg, Bronx, both of N.Y.

[73] Assignee: Ciba-Geigy Corporation, Ardsley, N.Y.

[22] Filed: Dec. 27, 1974

[21] Appl. No.: 536,771

Related U.S. Application Data

[62] Division of Ser. No. 325,712, Jan. 22, 1973, Pat. No. 3,862,151, which is a division of Ser. No. 842,377, July 16, 1969, Pat. No. 3,723,435.

[52] U.S. Cl. .................... 424/245; 252/DIG. 13; 252/106; 252/107; 260/45.75 R; 260/45.8 NW; 260/270 R; 260/283 BZ; 260/283 S; 424/DIG. 4; 424/258; 424/365; 260/45.75 B; 260/45.75 S; 260/45.75 V
[51] Int. Cl.² .................................. A61K 31/47
[58] Field of Search ............... 260/270 R; 424/245, 424/258, DIG. 4

[56] References Cited
UNITED STATES PATENTS

| | | | |
|---|---|---|---|
| 2,189,717 | 2/1940 | Scott | 260/283 S |
| 2,372,588 | 3/1945 | Larsen et al. | 424/258 X |
| 2,381,082 | 8/1945 | Shinkle | 424/258 |
| 3,088,916 | 5/1963 | Roman | 252/106 |
| 3,235,556 | 2/1966 | Wakeman et al. | 260/286 |
| 3,236,733 | 2/1966 | Karsten et al. | 424/245 |
| 3,555,030 | 1/1971 | Loev et al. | 424/258 X |

Primary Examiner—Jerome D. Goldberg
Assistant Examiner—Vera C. Clarke

[57] ABSTRACT

The invention relates to a method for combatting dandruff and anti-dandruff shampoos containing compounds having the structural formula in tautomeric form:

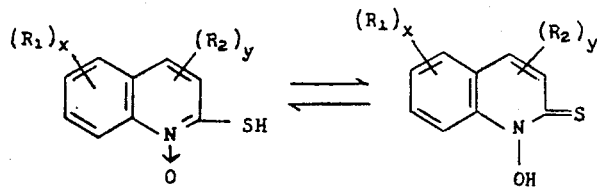

and metal salts and complexes thereof wherein $R_1$ and $R_2$ are hydrogen, alkyl, cycloalkyl, aryl, alkylthio, halogen, nitro, trifluoromethyl or alkoxy; $x$ is an integer from 1 to 4 and $y$ is an integer from 1 to 2.

12 Claims, No Drawings

COMBATTING DANDRUFF WITH MERCAPTO QUINOLINE N-OXIDES

This is a division of application Ser. No. 325,712, filed on Jan. 22, 1973, now U.S. Pat. No. 3,862,151, which is a division of application Ser. No. 842,377, filed July 16, 1969, now U.S. Pat. No. 3,723,435.

BACKGROUND OF THE INVENTION

The present invention relates to novel mercapto quinoline N-oxides, metal complexes thereof and the utilization of the latter in anti-dandruff shampoo compositions and in methods for combatting dandruff.

The precise cause of dandruff in the scalp area is at present unknown. It has been theorized that the skin particles normally shed from the scalp surfaces during the process of aging accumulate and combine with the oils exuded by the scalp to form a condition which enhances the growth of those bacteria, fungi, or other biological agents responsible for the propagation and accumulation of dandruff.

It is emphasized, however, that the above mechanism is at best an unproven theory. One of the major obstacles to a complete acceptance of this theory is the fact that many extremely powerful bactericides and fungicides have no effect whatsoever on the spread of dandruff in the human scalp. Moreover, substances such as elemental sulfur which are not recognized as having potent bactericidal and fungicidal activity are extremely effective in the control of dandruff. Obviously, then, factors other than bacteria and fungi contribute to the growth and spread of dandruff.

Accordingly, the selection of agents suitable for the control of dandruff is necessarily a hit and miss proposition. It is only by the process of trial and error that those skilled in the art have been able to provide the art with effective anti-dandruff agents to date.

One type of such anti-dandruff agent is described in U.S. Pat. No. 3,236,733. The compounds described therein as being useful for combatting dandruff are certain metal salts or complexes of 1-hydroxy-2-pyridinothione. Although providing a high degree of anti-dandruff activity, the metal salts of 1-hydroxy-2-pyridinethiones suffer from the disadvantage that they are slightly toxic, particularly when applied to the scalps of those individuals having unusually sensitive skin. Such individuals experience irritation and reddening of the skin and in certain cases, highly aggravated reactions in the form of open sores, etc., upon application of these thione salts to their scalps.

There exists in the prior art, therefore, the need for an anti-dandruff agent which is highly effective in combatting dandruff and, simultaneously, non-toxic to the scalp or skin.

Accordingly, it is an object of the present invention to provide novel chemical compounds having a high degree of anti-dandruff activity which are non-toxic to the skin or scalp.

It is further object of the present invention to provide an anti-dandruff shampoo composition which is non-toxic to the scalp or skin.

It is still a further object of the present invention to provide a method for combatting dandruff with a composition which is non-toxic to the scalp or skin.

SUMMARY OF THE INVENTION

The above and other objects of the present invention are achieved by the provision of novel mercapto quinoline N-oxides having the following structural formula in tautomeric form:

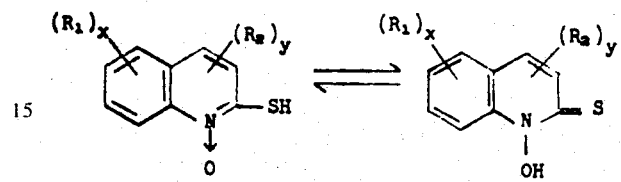

and salts and complexes thereof with metals non-toxic to the scalp or skin wherein $R_1$ and $R_2$ are independently selected from the group consisting of hydrogen, alkyl of 1 to 24 carbon atoms, cycloalkyl, aryl, alkylthio having 1 to 24 carbon atoms, halogen, nitro, trifluoromethyl and alkoxy of 1 to 4 carbon atoms; x is an integer from 1 to 4 and y is an integer from 1 to 2.

It has been found that metal complexes of the above mercapto quinoline N-oxides possess a high degree of anti-dandruff activity and are relatively non-toxic to the scalp and skin.

Shampoos containing the above-described mercapto quinoline N-oxide metal complexes and methods involving the application thereof to the scalp and hair have been found to be highly effective in controlling the propagation and spread of dandruff. At the same time, the application of these shampoo compositions to the scalp produce no toxic effects thereon, even in individuals having extremely sensitive skin.

DETAILED DESCRIPTION OF THE INVENTION

In the above tautomeric structural formula, $R_1$ and $R_2$ have been defined as hydrogen, alkyl, cycloalkyl, aryl, alkylthio, halogen, nitro, trifluoromethyl and alkoxy.

The preferred mercapto quinoline N-oxides are those wherein $R_1$ and $R_2$ are each H.

Among the alkyl substituents, the most preferred are the lower alkyl groups, i.e. having 1 to 4 carbon atoms, e.g. methyl, ethyl, n-propyl, iso-propyl, butyl. Higher alkyl substituents include by way of example dodecyl, tetradecyl, hexadecyl, octadecyl, eicosyl, docosyl, tetracosyl.

Suitable cycloalkyl substituents include by way of example cyclopentyl, methylcyclopentyl, ethylcyclopentyl, etc; chlorocyclopentyl, dichlorocyclopentyl, cyclohexyl, methylcyclohexyl, ethylcyclohexyl, etc., chlorocyclohexyl, dichlorocyclohexyl.

Exemplary of the aryl substituents are phenyl, o-tolyl, m-tolyl, p-tolyl, 2,3-dimethylphenyl, 2,4-dimethylphenyl, 2,5-dimethylphenyl, 2,6-dimethylphenyl, 3,4-dimethylphenyl, 3,5-dimethylphenyl, etc., 2-chlorophenyl, 3-chlorophenyl, 4-chlorophenyl, 2,3-dichlorophenyl, 2,4-dichlorophenyl, 2,5-dichlorophenyl, 2,6-dichlorophenyl, 3,4-dichlorophenyl, 3,5-dichlorophenyl, etc.

Suitable alkyl groups of the alkylthio and alkoxy substituents include those mentioned above; the most preferred being the lower alkyl groups.

Suitable halogen substituents include trifluoromethyl, fluoro, chloro, bromo and iodo; the most preferred being chloro.

Salts or complexes of the above described mercapto quinoline N-oxides with any metal which is non-toxic to the scalp or skin may be employed in the present invention. Suitable metals include lithium, sodium, potassium, zinc, calcium, tin, copper, antimony, lead, manganese, and aluminum.

The preferred metals are sodium and zinc; zinc being the most preferred. The most preferred anti-dandruff agent is the zinc complex of 2-mercapto-quinoline-N-oxide.

The terms 'salts or complexes' have been employed to define the metal derivatives of the 2-mercapto-quinoline-N-oxides of the present invention, the specific compound formed being determined by the valence of the metal M. The structure may be depicted thusly:

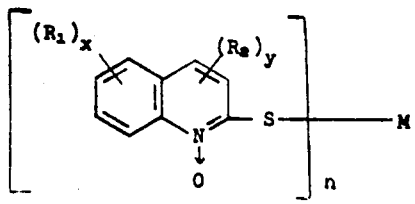

wherein $R_1$, $R_2$, $x$ and $y$ have the meanings given above; M is a metal and $n$ is the valence of said metal.

The compounds of the present invention may be prepared according to methods well known in the prior art. Generally, the following reaction scheme may be employed to prepare the compounds of the invention:

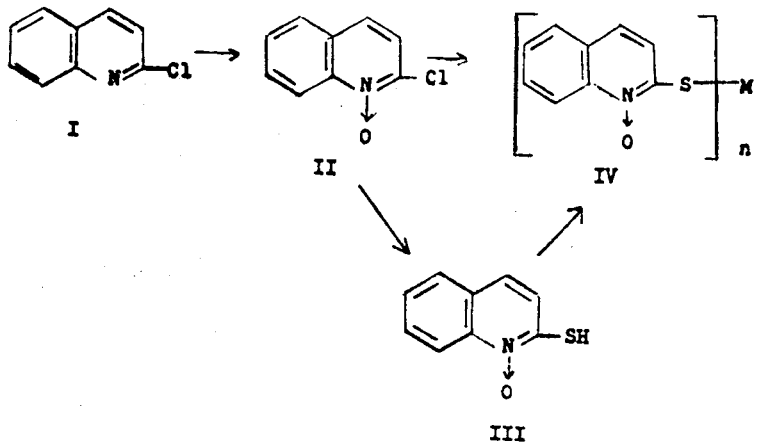

The starting materials (I) are well known in the prior art. They are described, e.g. in: C. A., vol. 54, pp. 24741 and 24742; C. A., vol. 55, p. 18728; C. A., vol. 51, p 1959; C. A., vol. 44, p. 632; C. A., vol. 41, p 2056; C. A., vol. 57, p 11832; C. A., vol. 58, p 13913; C. A., vol. 58, p 13744; C. A., vol. 59, pp. 8743 and 97432; J. A. C. S., vol. 64, p 1357.

The starting materials (I) are converted to the N-oxides by methods well known in the prior art; e.g. by contacting with a per-acid such as per-maleic acid in a suitable solvent.

The intermediate 2-chloro-quinoline-N-oxide (II) may be converted to the 2-mercapto-quinoline-N-oxide (III) or directly to the metal salt or complex thereof (IV). The mercapto compound may be obtained by reacting the chloro derivative with a mixture of NaSH and $Na_2S$ in the presence of an acid.

Optionally, the metal salt or complex may be prepared directly by reacting the chloro derivative with MSH in the presence of a proton acceptor solvent. It is to be understood that mixtures of complexes of various metals with 2-mercapto-quinoline-N-oxide may be prepared by reacting the chloro derivative with a mixture of metal salts. Moreover, the metal complexes may be converted to complexes of other metals by reaction with salts of metals which are lower on the EMF scale.

Also, the mercapto-quinoline-N-oxides (III) may be converted to the metal complex (IV) by reaction with the appropriate metal salt.

The anti-dandruff agents of the present invention may be incorporated in any of the shampoo compositions well known in the prior art. Generally, shampoo compositions comprise aqueous detergent bases in liquid or paste form containing conventional shampoo additives such as coloring agents, perfume, fillers, thickeners, solvents, opacifiers, builders, conditioning agents such as amine oxide surfactants, lanolin derivatives, preservatives, buffers, anti-static agents, etc. The shampoos generally contain from about 1% to about 30% by weight of a detergent.

The detergents may be anionic, cationic, amphoteric or non-ionic. Suitable anionic detergents include by way of example propylated naphthalenesulfonic acid, sodium alkylnaphthalenesulfonate, sulfonated monoglyceride of coconut fatty acids, sodium oleyl sulfate.

Suitable examples of cationic, detergents include lauryltrimethylammonium chloride, cetyltrimethylammonium bromide, cetyldimethylammonium bromide.

Suitable amphoteric detergents include N-alkyl taurines, such as N-dodecyl, taurine, alkyl α-alanines such as dodecyl β-alanine, long chain alkyl amino sulfonic acids, alkyl sulfonamides and the like.

Among the non-ionic detergents which may be employed in the shampoo compositions of the present invention may be mentioned by way of example polyethylene glycol lauryl ether, polyethylene esters of fatty acids or rosin acids, polyethylene glycol stearate, sorbitan monopalmitate, sorbitan monooleate.

The anti-dandruff agents of the present invention may be incorporated in the above shampoo compositions in amounts sufficient to provide effective anti-dandruff control on the hair and scalp. Generally, amounts ranging from about 0.1 to about 10% by weight are included.

It has been found that the anti-dandruff agents of the present invention are highly substantive to the scalp and hair, ie., is retained on the scalp and in the hair despite rinsing and builds up a layer thereof on the scalp and in the hair upon repeated use. By applying the above shampoos to the scalp and hair, the propagation and spread of dandruff may be effectively controlled.

Because of their microbiological activity, the salts and complexes of the present invention may be beneficially incorporated into other products where antibacterial or fungicidal activity is desired such as antibacterial and deodorant toilet soaps, including detergents and combinations of detergents and soaps; laundry detergents and soaps; other laundry finishing compositions such as softeners, acid sours, antichlors and both natural and synthetic starches; in hard surface disinfecting compositions such as floor and wall cleaners; various personal products such as creams, powders, talcs and aerosol sprays; in water treatment, secondary oil recovery and heat exchanges, polymers such as plasticized polyvinyl chloride and the like for the prevention of microbiocidal deterioration; and in paints and coatings in both oil base and latex types or in can preservation and in improving weatherability.

The following non-limiting examples are illustrative of methods for the preparation of the anti-dandruff agents of the invention.

EXAMPLE 1 a. 420 g of maleic anhydride was dissolved in 900 ml of chloroform and cooled. 84 g of 30% hydrogen peroxide was added dropwise thereto with stirring in an ice bath. The mixture was stirred at 0°–5°C for 1–2 hours. 49.2 g of 2-chloroquinoline in 90 ml of chloroform was added dropwise thereto with stirring in an ice bath at 0°–5°C over 1.5 hours. The resulting mixture was stirred overnight at 0°–5°C and stored at 5°C. for 10 days. The mixture was then filtered, yielding 479.1 g of a precipitate having an melting point of 141°–5°. The filtrate was stripped to yield 99.7 g of residue which was dissolved in chloroform and passed through a bed of 2100 g of neutral alumina and eluted with chloroform. 12 × 200 ml fractions were obtained followed by 12 × 450 ml fractions. The product fractions (8–14) were combined and stripped to yield 28.0 g of residue. The residue was placed in a freezer and previously prepared seeds were added which induced solidification of the product. A sample of the purified product was dried to constant weight at 55°/0.1 mm. It had a melting point of 84°–8° and gave satisfactory elemental analysis.

Analysis for $C_9H_6ONCl$: Calc.: C, 60.18; H, 3.36; N, 7.80; Cl, 19.73; Found: C, 60.40; H, 3,85; N, 7.88; Cl, 20.01 C, 60.14; H, 3.71; H, 7.86.

b. 840 g of maleic anhydride was dissolved in 1800 ml of chloroform at 40°–50°C and the mixture transferred to a 3000 ml, 3-neck flask equipped with a stirrer, condenser, thermometer and dropper funnel. While cooling in an icebath, 168 g of hydrogen peroxide (30%) was added to the mixture dropwise over 1.5 hours. While maintaining the temperature of the mixture at 5°–10°C, 88.4 g of 2-chloro-quinoline (dissolved in 250 ml of chloroform) was added thereto dropwise with stirring over 1 hour. The reaction was continued with stirring for 3 hours at 5°–10°C. The reaction mixture was transferred to a refrigerator and stored for 6 days.

The precipitate was filtered from the reaction mixture and washed with chloroform to yield 910 g of insoluble material. The filtrate was placed in a 4-liter separatory funnel and washed with 1000 ml of a 10% solution of potassium carbonate. The wash solution was separated therefrom and the filtrate again washed with 500 ml of a 10% potassium carbonate solution. The product contained in the chloroform layer was separated and placed in a refrigerator over solid potassium carbonate to dry overnight.

The chloroform solution was then passed through a layer of neutral alumina on a sintered glass funnel under light suction to remove potassium carbonate and water. A clear chloroform solution was obtained. The alumina was washed with 200 cc of chloroform and combined with the original filtrate. The combined solutions was stripped on a rotary evaporator keeping the temperature below 40°C. to yield a dark colored syrupy residue. The residue was treated with 250 ml of anhydrous ethyl ether. The resulting mixture was shaken with 100 ml of water for 5 minutes to yield a copious light colored precipitate. The mixture was cooled to 5°–10°C and filtered. The precipitate was washed with 200 ml of water followed by washing with 200 ml of ethyl ether. The precipitate was then dried over phosphorus pentoxide in a dessicator, under vacuum for 5 days to yield 48.7 g (51.4% yield) of product having a melting point of 77°–84°C. Comparison by thin layer chromatography using silica gel (absorbent), 4:1 benzene-methanol (developer) and iodine (detector) indicated identity with the previously prepared product.

EXAMPLE 2

Preparation of 2-Mercapto-Quinoline-N-Oxide 30.5 g of 2-chloro-quinoline-N-oxide and 850 ml of water were added to a 2-liter flask equipped with a stirrer, condenser, thermometer and dropping funnel. The mixture was heated with stirring to 45°C. 5.8 g of sodium hydrosulfide (50% assay) and 41.7 g of sodium sulfide (32.5% assay) in 155 ml of water were added to the dropping funnel and added dropwise over 2 hours, to the contents of the flask while heating at 65°C for 45 minutes. The reaction mixture which was completely in solution was cooled to room temperature. A solution of 70 g of concentrated hydrochloric acid in 70 ml of water was placed in a dropping funnel and added dropwise to the reaction mixture with stirring. Hydrogen sulfide evolved from the reaction mixture was collected in a 20% NaOH trap. After 1 hour sufficient hydrochloric acid solution was added to bring the pH of the reaction mixture to 1.0. The copious precipitate deposited from the reaction mixture was filtered on a sintered glass funnel, washed with 700 ml of water and dried overnight under vacuum. The product weighed 19.0 g (63.2% yield), had a melting point of 65°–67°C. and was identified by infrared spectroscopy to be 2-mercapto-quinoline-N-oxide.

Using procedures analogous to those of this example employing equivalent amounts of the appropriate starting materials, other compounds falling within the scope of the present invention are readily prepared.

EXAMPLE 3

Preparation of the Sodium Complex Of 2-Mercapto-Quinoline-N-Oxide a. A mixture of 1.8 g of 2-chloro-quinoline-N-oxide, 1.1 g of sodium hydrosulfide and 10 ml of dimethylformamide was heated on a steam bath for 1 hour and allowed to stand overnight. The reaction mixture was stripped to dryness to remove dimethylformamide. Approximately 25 ml of ethyl alcohol was added and the mixture filtered to remove a small amount of a white precipitate of NaCl. The filtrate was stripped and gave 2.3 g residue. This residue (R1) was triturated with benzene which left a new residue (R2) of 1.0 g having a melting point of 235°–250°. This was recrystallized from a mixture of acetone (60 ml) and heptane (60 ml) and afforded 0.8 g of product. After drying overnight at 65°/0.2 mm, it had a melting point of 255–260° (dec.). A neutral equivalent established that the product was the sodium salt of 2-mercapto-quinoline-N-oxide.

EXAMPLE 4

Preparation of Zinc Complex of 2-Mercapto-Quinoline-N-Oxide a. 1.5 g of 2-mercapto-quinoline-N-oxide, 0.68 g of 50% NaOH solution and 20 ml of water were mixed and vigorously stirred. The insoluble matter was filtered off. The filtrate was back-titrated with dilute hydrochloric acid to a pH of 9.0. With continuous vigorous stirring a solution of 1.26 g of zinc chloride in 20 ml of water was added dropwise to the filtrate to give a copious light green-yellow precipitate. The precipitate was collected by filtration, washed twice with 30 ml portions of water, once with 20 ml of ethanol and once with 20 ml of anhydrous ethyl ether. The precipitate of the zinc complex of 2-mercapto-quinoline-N-oxide was then dried under vacuum at 56°C at 2 mm for 2 hours to give 1.7 g (96.2% yield) having a melting point of 243–46° (dec.).

b. 17.7 g of 2-mercapto-quinoline-N-oxide was added portion wise over ½ hour to 8.8 g of sodium hydroxide in 250 ml of water with stirring to yield a mixture having a pH of 12. The insoluble matter was filtered off and the filtrate back-titrated with dilute HCl to a pH of 9.0–9.5. A solution of 13.63 g of zinc chloride in 200 ml of water was added portionwise to the filtrate with vigorous stirring to give a copious precipitate of the zinc complex of 2-mercapto-quinoline-N-oxide. The product was product was filtered and washed twice with 200 ml of water, once with 200 of ethanol and once with 200 ml of anhydrous ethyl ether. The product was dried under vacuum (2mm) over phosphorous pentoxide for 17 hours to give 19.6 g (94% yield); melting point 244°–46°.

Analysis for Calc.: C, 51.74; H, 2,90; S, 15.35; N, 6.71; Zn, 15.65; Found: C, 51.26; H, 3.00; S, 14.46; N, 6,56; Zn, 15.76 C, 51.28; H, 2.93; S, -----; N, 6.67; Zn, 15.80.

c. A clear solution of 68.1 mg zinc chloride in 10 ml of water was added to a clear solution of 199 mg of the sodium complex of 2-mercapto-quinoline-N-oxide in 5 ml of water with swirling. The resulting tan precipitate was filtered, washed successively with 3 × 15 ml portions of water, 2 × 15 ml portions of ethanol and 2 × 15 ml portion. product was air dried, then dried to constant weight at 110° at 0.1 mm. This afforded 170 mg of product having a melting point of 250° (dec.).

d. A clear solution of 1.02 g of zinc chloride in 125 ml of water was added to a clear solution of 3.32 g of the sodium complex of 2-mercapto-quinoline-N-oxide in 100 ml of water with stirring. After 15 minutes of stirring, the resulting precipitate of the zinc complex of 2-mercapto-quinoline-N-oxide was filtered, washed successively with 3 × 50 ml portions of water, 4 × 25 ml portions of ethanol and 6 × 25 ml portions of anhydrous ethyl ether, and air dried. The product (2.8 g — 90% yield) had a melting point of 250°–260° (dec.). Following drying in a vacuum oven at 90°–100°/0.3 mm for 2 hours, the product had a melting point of 240°–250° (dec.).

Analysis for Calc.: N, 6.70; S, 15.34; Zn, 15.64; Found: N, 6.58; S, 14.61 ±0.03; Zn, 15.53 ±0.23

The foregoing procedures are employed to prepare salts or complexes of the other metals (M) listed above.

As stated above, the 2-mercapto-quinoline-N-oxide metal complexes of the present invention have an effectiveness against dandruff comparable to that of the metal complexes of the hydroxy-pyridinethiones of U.S. Pat. No. 3,236,733 but are comparatively less toxic to the scalp and skin.

The following examples illustrate the effectiveness of the compositions of the invention in controlling dandruff.

EXAMPLE 5

The microbiological activities of the zinc and sodium complexes of 2-mercapto-quinoline-N-oxide (MQNO) against P. Ovale were compared with the sodium and zinc salts of pyridinethione-N-oxide (PTO) and other conventional soapbacteriostats. P. Ovale is a microorganism associated with dandruff conditions.

Equal amounts of the respective compounds were dissolved in methyl cellosolve, dimethylformamide, or water, serially diluted in ten fold sequence and incorporated into plates of molten Agar. The plates were allowed to solidify, were then inoculated with P. Ovale (ATCC 14521), incubated at 27°C. for 4 days and inspected for growth. The results are set forth in Table I.

TABLE 1

Activity of Various Antimicrobial Agents Against P. Ovale

| Compounds | MIC* in PPM |
|---|---|
| Zn MQNO | 50–60 |
| Na MQNO | 50–60 |
| Zn PTO | 7–10 |
| Na PTO | 7–10 |
| 2-mercaptoquinoline | >1000 |
| 2-mercaptopyridine | >1000 |
| Tetrachloro salicyanilide | 1000 |
| Trichloro salicyanilide | >1000 |
| Tribromo salicyanilide | 1000 |
| Hexachlorophene | >1000 |
| Trichlorocarbanilide | >1000 |
| 2,2'-dihydroxy-5.5'-dichlorodiphenyl monosulfide | >1000 |
| Thio bis(dichlorophenol) | >1000 |
| P-chloro-m-xylenol | 1000 |
| 5-chloro-6-bromobenzoxazo-linone | 1000 |
| 50% m-alkyldimethyl ethyl-benzyl ammonium chloride-50% m-alkyl dimethyl-benzyl ammonium chloride | >1000 |
| m-alkyl-dimethyl-ethyl-benzyl ammonium chloride | >1000 |
| Benzethonium chloride | >1000 |
| N-alkyl-dimethyl-benzyl ammonium chloride | >1000 |
| N-alkyl-dimethyl-ethyl-benzyl ammonium cyclohexyl sulfamate | >1000 |
| Undecylenyl polypeptide | >1000 |
| Sodium salt of sulphosuccinate of undecylenic-monoalkylolamide | >1000 |

TABLE 1-continued

Activity of Various Antimicrobial Agents Against P. Ovale

| Compounds | MIC* in PPM |
|---|---|
| Diiodohydroxyquinoline | 1000 |
| 8-Hydroxyquinoline | 100 |
| Undecylenic acid | 1000 |
| Undecen-1-ol | >1000 |

*Minimum Inhibitory Concentration

It is apparent from the results of Table 1 that the activity of the compositions of the present invention are comparable to that of the pyridinethione-N-oxides of U.S. Pat. No. 3,236,733. It is also apparent that the other conventional bacteriostats, fungistats and quaternary ammonium compounds are totally void of activity or are vastly inferior to the compositions of the invention.

EXAMPLE 6

The substantivity/activity of the zinc complex of 2-mercapto-quinoline-N-oxide of the invention in calf-skin were compared with the zinc salt of pyridinethione-N-oxide in the following manner. ZnMQNO and ZnPTO were incorporated by blending on a 3-roll mill in amounts of 1% and 2% by weight into a non-bacteriostatic paste shampoo of the following composition.

| | |
|---|---|
| Long chain modified alkanolamide, anionic | 25.4% |
| Lauric acid | 11.9% |
| Coconut alkanolamide, non-ionic | 1.9% |
| Triethanolamine salt of lauroyl sulfate | 1.9% |
| Trisodium hydroxyethyl ethylenediamine triacetate (41% solution) | 1.1% |
| Water | 57.8% |
| | 100.0% |

Calf skin specially prepared by the method of Vinson IN VITRO TESTS FOR MEASURING ANTIBACTERIAL ACTIVITY OF TOILET SOAP AND DETERGENT BARS by L. J. Vinson, E. L. Ambye, A. G. Bennet, Journal of Pharmaceutical Sciences, Vol. 50, P. 10, October, 1961.

0.3 g of shampoo was applied in each instance to 12.5 sq. in. of calf skin (equivalent to 3.5 g of shampoo per 90.2 sq. in. of human scalp) and a rich lather worked up for 2 minutes. The calf skin was then rinsed in running tap water for 30 seconds with vigorous message to remove all lather. The moist skin was then given a second lather identical to the first and again rinsed as before. After air drying, the calf skins were cut into 2.1 cm discs and placed on agar inoculated with P. Ovale. After 4 days incubation at 27°C, the zones of inhibition size were recorded. The results are set forth in Table 2.

It is apparent from these results that the substantivity and activity of the compositions of the invention are comparable to those of the agents described in U.S. Pat. No. 3,236,733. It should be noted that the smaller zone size produced by ZnMQNO does not indicate a lesser activity than ZnPTO since zone size is largely dependent upon diffusion characteristics in agar. since ZnMQNO is less soluble than ZnPTO it would be expected to exhibit a smaller zone size.

The following example illustrates the antimicrobial spectrum of the compositions of the invention as compared with those of U.S. Pat. No. 3,236,733.

EXAMPLE 7

Equivalent amounts of ZnMQNO, NaMQNO, ZnPTO and NaPTO were solubilized in methyl cellosolve (PTO) and dimethyl formamide (MQNO). Ten fold serial dilutions were prepared employing additional solvent and equal aliquots pipetted into molten (50°C) agar support media. Nutrient Agar was employed for all bacteria and Mycological Agar was employed for the fungi and dermatophyte. After preparing pour plates for the bacteria and streaks for the fungi and dermatophyte, the plates were incubated (37°C and 27°C, respectively) and observed for growth. The results are set forth in Table 3.

As is apparent from these results, zinc and sodium PTO may be classed as broad-spectrum antimicrobial agents showing good activity at low concentrations against Gram-positive and negative bacteria, fungi and dermatophytes.

Table 2

| Replicate Plates | Zone of Inhibition Against P. Ovale - Calf Skin | | | |
|---|---|---|---|---|
| | 2% Zinc PTO[1] | | 2% MQNO[2] | |
| | 1 Application | 2 Applications | 1 Applicaton | 2 Applications |
| 1 | 4.5 | 10.0 | 0.5 | 2.0 |
| 2 | 4.0 | 7.0 | 1.5 | 4.5 |
| 3 | 5.0 | 10.0 | 1.5 | 2.0 |
| 4 | 4.0 | 5.0 | 1.0 | 2.5 |

[1] Zinc pyridienthione-N-oxide from commercial 'Head and Shoulders' shampoo
[2] Zinc 2-mercaptoquinoline-N-oxide from formulated paste shampoo as described in Example 6.

Table 3

| Organisms | ATCC No. | Minimum Inhibitory Concentration in PPM | | | | | | | |
|---|---|---|---|---|---|---|---|---|---|
| | | NaPTO | | ZnPTO | | NaMQNO | | ZnMQNO | |
| Staph. aureus[1] | 6538 | 0.1 | 1.0 | 0.1 | 1.0 | 0.1 | 1.0 | 0.1 | 1.0 |
| E. Coli[1] | 4352 | 1.0 | 10 | 1.0 | 10 | 1.0 | 10 | 1.0 | 10 |
| Proteus vulgaris[2] | 9920 | 1.0 | 10 | 1.0 | 10 | 0.1 | 1.0 | 1.0 | 10 |
| Aspergillus oryzae[3] | 10196 | 10 | 100 | 10 | 100 | 10 | 100 | 10 | 100 |
| T. interdigitale[4] | 9533 | 1.0 | 10 | 1.0 | 10 | 1.0 | 10 | 10 | 100 |

[1] The strains of Staph. aureus and E. Coli employed are the official test organisms used in AATCC Test method 90-1965T.
[2] Proteus vulgaris 9920 is a strong ammonia producer and employed by many organizations to test treated diapers.
[3] Aspergillus oryzae 10196 is employed by industry and the U.S. Army to test the degradation of paint films in tropical chambers.
[4] Trichophyton interdigitale 9533 is used for germicide testing in the U.S. and included by the USDA for testing the fungicidal activity of aerosol hard-surface cleaners.

What is claimed is:

1. An anti-dandruff shampoo comprising an aqueous detergent base in liquid or paste form and an amount sufficient to provide effective anti-dandruff control on the hair and scalp of a salt or complex of a metal selected from the group consisting of lithium, sodium, potassium, zinc, calcium, tin, copper, antimony, lead, manganese, and aluminum of a compound having the following structural formula in tautomeric form:

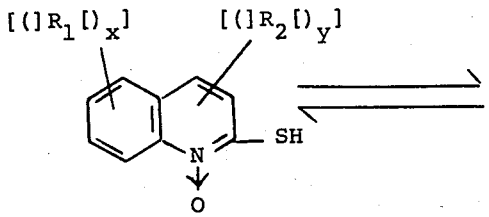
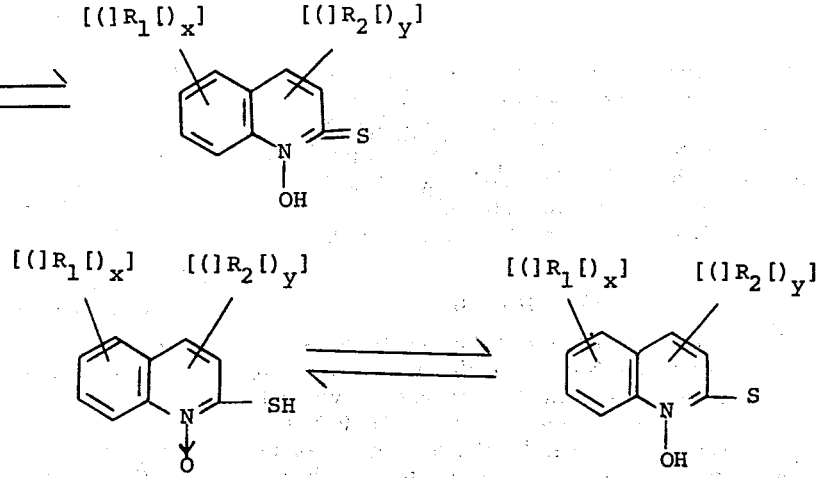

wherein $R_1$ and $R_2$ are each independently selected from the group consisting of hydrogen, alkyl of one to 24 carbon atoms, phenyl, phenyl substituted with chlorine or methyl, halogen, trifluoromethyl and alkoxy of one to four carbon atoms.

2. The anti-dandruff shampoo of claim 1 wherein said compound has the following structural formula in tautomeric form:

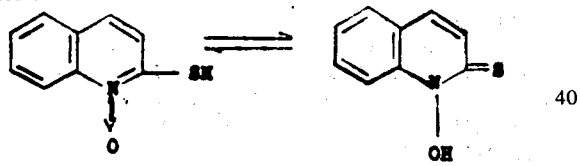

3. The anti-dandruff shampoo of claim 2 wherein said metal is selected from the group consisting of sodium and zinc.

4. The anti-dandruff shampoo of claim 2 wherein said metal is zinc.

5. The anti-dandruff shampoo of claim 2 wherein said metal is sodium.

6. The anti-dandruff shampoo of claim 2 wherein said metal complex is present in an amount of from about 0.1% to about 10% by weight, based on the weight of said detergent composition.

7. A method for combatting dandruff comprising applying to the hair and scalp a shampoo comprising an aqueous detergent base in liquid or paste form and an amount sufficient to provide effective anti-dandruff control of a salt or complex of metal selected from the group consisting of lithium, sodium, potassium, zinc, calcium, tin, copper, antimony, lead, manganese, and aluminum of a compound having the following structural formula in tautomeric form:

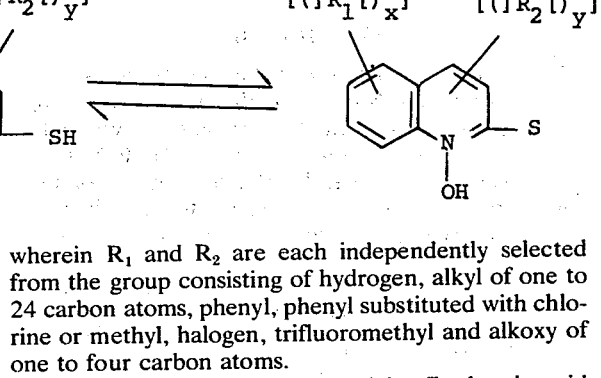

wherein $R_1$ and $R_2$ are each independently selected from the group consisting of hydrogen, alkyl of one to 24 carbon atoms, phenyl, phenyl substituted with chlorine or methyl, halogen, trifluoromethyl and alkoxy of one to four carbon atoms.

8. The method according to claim 7 wherein said compound has the following structural formula in tautomeric form:

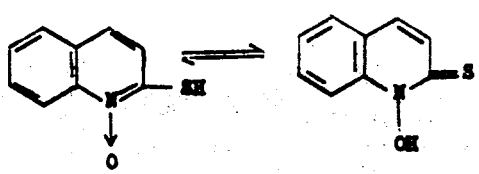

9. The method according to claim 7 wherein said metal is selected from the group consisting of sodium and zinc.

10. The method according to claim 7 wherein said metal is zinc.

11. The method according to claim 7 wherein said metal is sodium.

12. The method according to claim 7 wherein said metal complex is present in an amount of from about 0.1% to about 10% by weight.

* * * * *